US007267968B2

(12) United States Patent
Carnell et al.

(10) Patent No.: US 7,267,968 B2
(45) Date of Patent: Sep. 11, 2007

(54) MICROBIAL N-AND O-DEMETHYLATION OF A THEBAINE DERIVATIVE

(75) Inventors: Andrew John Carnell, Liverpool (GB); John Alfred Davis, Hull (GB)

(73) Assignee: Reckitt Benekiser Healthcare (UK) Limited, Slough, Berkshire (GB)

( * ) Notice: Subject to any disclaimer, the term of this patent is extended or adjusted under 35 U.S.C. 154(b) by 500 days.

(21) Appl. No.: 10/512,746

(22) PCT Filed: Apr. 24, 2003

(86) PCT No.: PCT/GB03/01735

§ 371 (c)(1),
(2), (4) Date: Oct. 27, 2004

(87) PCT Pub. No.: WO03/095458

PCT Pub. Date: Nov. 20, 2003

(65) Prior Publication Data

US 2005/0164358 A1    Jul. 28, 2005

(30) Foreign Application Priority Data

May 10, 2002  (GB) ................................. 0210638.3

(51) Int. Cl.
*C12P 17/18* (2006.01)
*C12N 1/16* (2006.01)
(52) U.S. Cl. .................................. 435/119; 435/254.1
(58) Field of Classification Search ...................... None
See application file for complete search history.

(56) References Cited

U.S. PATENT DOCUMENTS 3,433,791 A    3/1969    Bentley ...................... 260/285

FOREIGN PATENT DOCUMENTS

CH             558 362 A       12/1974
FR             2 554 816 A     5/1985
WO             WO89/00203 A1   1/1989
WO             WO97 44317 A    11/1997

OTHER PUBLICATIONS

International Search Report dated Jul. 23, 2003 for Application No. PCT/GB03/01735.
International Preliminary Examination Report dated Dec. 29, 2003 for Application No. PCT/GB03/01735.
Combined Search and Examination Report from The Patent Office in Great Britain dated Oct. 17, 2002 for Application No. GB 0210638.3.
Shanghui Hu et al.; "Microbial Transformation of Taxoids: Selective Deacetylation and Hydroxylation of 2α, 5α, 10β, 14β-Tetra-acetoxy-4(20), 11-taxadiene by the Fungus *Cunninghamella echinulata*"; Tetrahedron.; vol. 52; No. 26; pp. 8739-8746; 1996; XP004103817; Elsevier Science Publishers, Amsterdam, NL; ISSN: 0040-4020.
J. Marton et al.; "Herstellung von 6,14-Ethenomophinan-Derivaten"; Monatshefte Fuer Chemie.; vol. 125; pp. 1229-1239; 1994; XP002208720; Springer Verlag, Vienna, At; ISSN: 0026-9247.

*Primary Examiner*—Samuel Barts
(74) *Attorney, Agent, or Firm*—Norris McLaughlin & Marcus, PA

(57) ABSTRACT

The invention provides a process for the N-demethylation or the N- and O-demethylation of a thebaine derivative which process comprises fermenting the derivative with a biocatalyst selected from the filamentous fungi from
*Cunninghamella dalmatica* NRRL 1394,
*Cunninghamella echinulata* NRRL 1387,
*Cunninghamella echinulata* NRRL 1384,
*Cunninghamella echinulata* ATCC 36190,
*Cunninghamella echinulata* ATCC 11585a,
*Cunninghamella echinulata* ATCC 9244,
*Cunninghamella polymorpha* NRRL 1395, or
*Rhizopus nigricans* Z5/1
in a basal fermentation medium at a temperature of at least 25° C. and not more than 34° C., for a period of time of at least 3 days.

13 Claims, No Drawings

MICROBIAL N- AND O-DEMETHYLATION OF A THEBAINE DERIVATIVE

The present invention relates to the synthesis of intermediate compounds which are useful in the synthesis of the alkaloid buprenorphine and, in particular, the synthesis of useful intermediates by the selective microbial N- and O-demethylation of 7a-[(S)-1-hydroxy-1,2,2-trimethylpropyl]-6,14-endo-ethano-6,7,8,14-tetrahydrothebaine.

The alkaloid buprenorphine, (chemical name 21-cyclopropyl-7a-[(S)-1-hydroxy-1,2,2,-trimethylpropyl]-6,14-endo-ethano-6,7,8,14-tetrahydrooripavine), is a commercially available mixed agonist/antagonist of μ receptors and can be synthesized relatively efficiently from the alkaloid thebaine. However, two steps in the synthesis involve the N- and O-dealkylation of thebaine derivatives and require the use of expensive and difficult to handle reagents, or lead to poor yields.

Accordingly, a target in improving the synthesis of buprenorphine from thebaine is an improved process for carrying out the dealkylation steps.

We have now discovered that certain filamentous fungi exhibit regiospecific N- and O-demethylation of a thebaine intermediate currently used in the synthesis of buprenorphine.

Accordingly, the present invention provides a process for the N-demethylation or the N- and O-demethylation of the compound of the formula

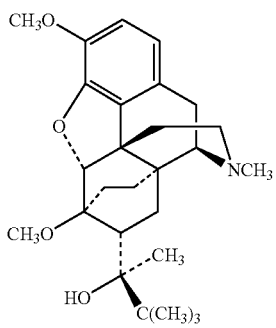

(I)

which process comprises fermenting the said compound of Formula I with a biocatalyst selected from the filamentous fungi
*Cunninghamella dalmatica* NRRL 1394,
*Cunninghamella echinulata* NRRL 1387,
*Cunninghamella echinulata* NRRL 1384,
*Cunninghamella echinulata* ATCC 36190,
*Cunninghamella echinulata* ATCC 11585a,
*Cunninghamella echinulata* ATCC 9244,
*Cunninghamella polymorpha* NRRL 1395, or
*Rhizopus nigricans* Z5/1 in a basal fermentation medium at a temperature of at least 25° C., preferably at least 27° C., most preferably at least 28° C. and not more than 34° C., preferably not more than 33° C. and most preferably not more than 32° C. for a period of time of at least 3 days, preferably at least 4 days.

The preferred filamentous fungi for use in the present invention is *Cunninghamella echinulata* NRRL 1384. The fermentation process is preferably carried out for a period of time of from 7 to 10 days and the fermentation medium is preferably vigorously shaken or stirred in order to assist the biotransformation process. The fermentation preferably takes place at a pH in the range of from 5 to 6.

The compounds which are produced by the N-demethylation or N- and O-demethylation process of the present invention are as follows:

N- and O-demethylation

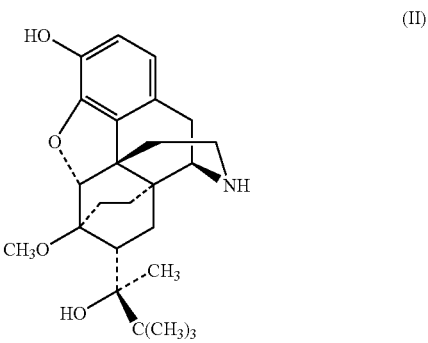

(II)

7a-[(S)-1-hydroxy-1,2,2-trimethylpropyl]-6,14-endo-ethano-6,7,8,14-tetrahydronororipavine N-demethylation

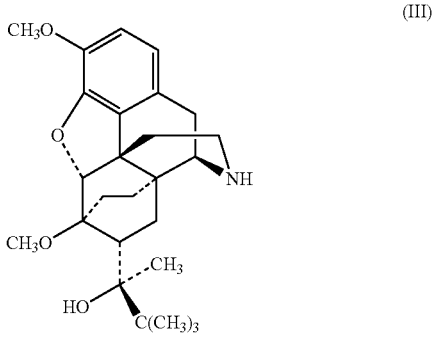

(III)

7a-[(S)-1-hydroxy-1,2,2-trimethylpropyl]-6,14-endo-ethano-6,7,8,14-tetrahydronorthebaine These products which are produced in the biotransformation process of the present invention may be isolated by procedures known in the art for example by chromatography, crystallisation or extraction procedures.

The compound of formula II may be directly converted to buprenorphine by N-alkylation, for example with a cyclopropylmethylhalide, in order to introduce a cyclopropylmethyl group onto the N-atom.

The compound of formula III may be converted to buprenorphine in two stages. The first stage comprising an N-alkylation, for example with a cyclopropylmethyl halide, in order to introduce a cyclopropylmethyl group onto the N-atom, and the second stage comprising the O-demethylation of the intermediate compound IV produced from the first stage by techniques well known in the art, for example using potassium hydroxide in diethylene glycol at an elevated temperature in the range of 200 to 245° C. These reaction schemes are shown in Scheme 1 below:

SCHEME 1

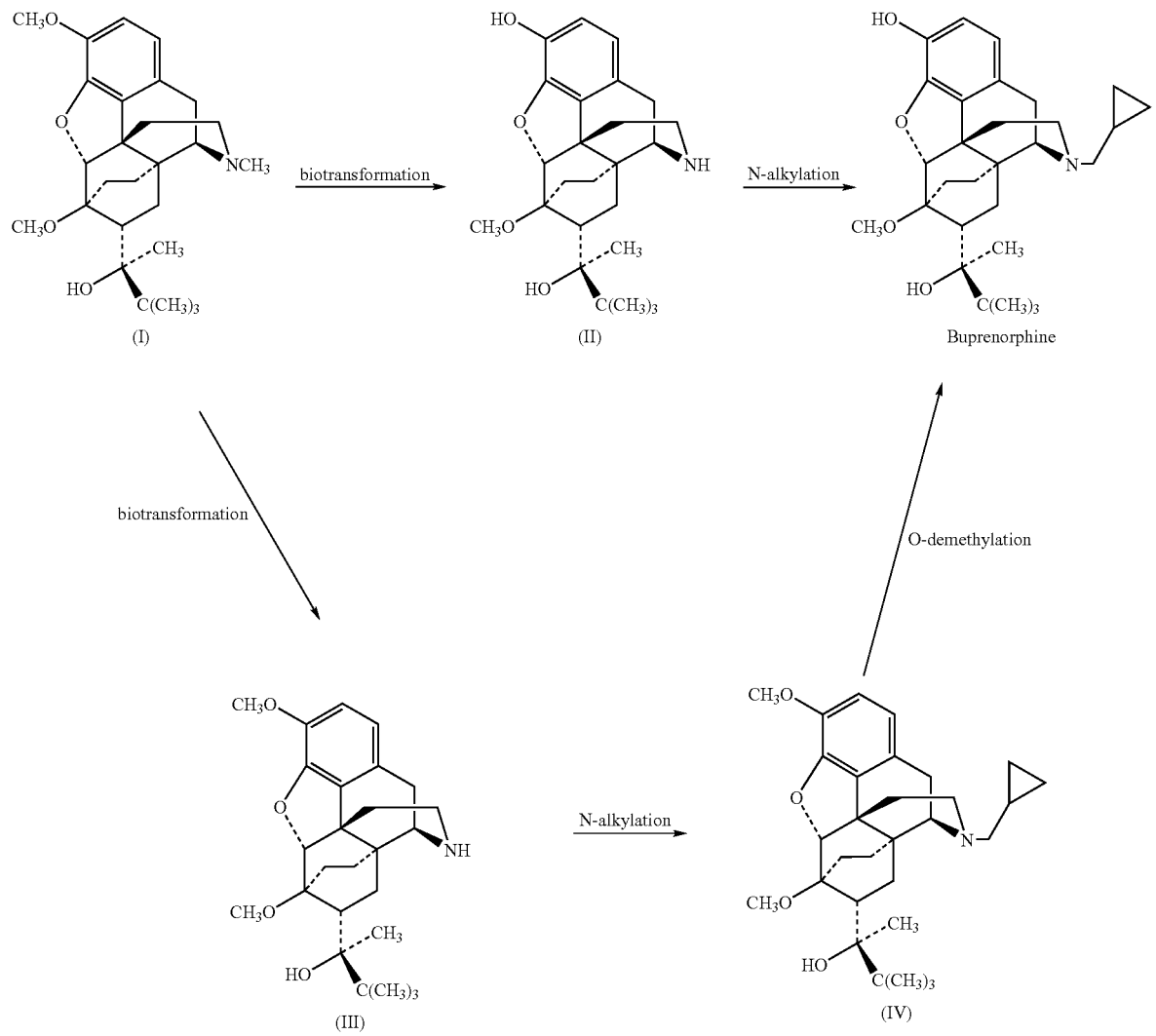

The present invention also includes within its scope a process for the preparation of buprenorphine from the compound of formula I, which process includes the step of the N-demethylation or the N- and O-demethylation of a compound of the formula

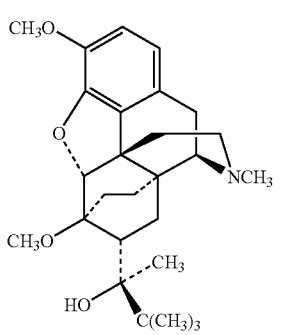

(I)

which process comprises fermenting the said compound of Formula I with a biocatalyst selected from the filamentous fungi

*Cunninghamella dalmatica* NRRL 1394,
*Cunninghamella echinulata* NRRL 1387,
*Cunninghamella echinulata* NRRL 1384,
*Cunninghamella echinulata* ATCC 36190,
*Cunninghamella echinulata* ATCC 11585a,
*Cunninghamella echinulata* ATCC 9244,
*Cunninghamella polymorpha* NRRL 1395, or
*Rhizopus nigricans* Z5/1 in a basal fermentation medium at a temperature of at least 25° C., preferably at least 27° C., most preferably at least 28° C. and not more than 34° C., preferably not more than 33° C. and most preferably not more than 32° C. for a period of time of at least 3 days, preferably at least 4 days.

The conversion of the N-demethylated or the N- and O-demethylated compounds of Formula II and Formula III as described above may be carried out by the processes as described above.

The present invention will be further described with reference to the following Examples.

EXAMPLES 1 TO 8

A total of 38 fungal type strains, 6 unknown fungal isolates from environmental samples and 2 strains of *S. cerevisciae* were tested for their ability to demethylate the compounds of formula I described above. Each organism was scored according to the number and intensity of the spots observed on thin layer chromatograms.

Eight candidate strains were selected for further testing. The compound of Formula I was subjected to biotransformation using each of the eight fungal strains under standard conditions as follows:

Standard biotransformation procedure: All organisms were grown in liquid fermentation media (50 ml) at 25° C. for 7-10 days with vigorous shaking (250 rpm) in a New Brunswick Scientific orbital incubator. The fungal fermentation medium consisted of 2% (w/v) glucose, 0.5% (w/v) Corn Steep Solids, pH6.2. After all biotransformations were complete the media were sampled (1 ml) and extracted with an equal volume of ethyl acetate. The extent of alkaloid demethylation was assessed by thin layer chromatography (TLC) in a solvent system comprising ethyl acetate::triethylamine (19:1) and developed with a CAN dip. Quantitative analysis of putative positive results was carried out by HPLC (Waters 2690 separations module, 996 photo-diode array). Samples were prepared as above, dried under a stream of $N_2$ gas and re-dissolved n a methanol based mobile phase (methanol, 600 ml; ammonium acetate, 1 g; distilled water, 160 ml; 0.1M acetic acid, 1 ml). Reverse phase HPLC was performed on an ODS-A column (250 mm×4.6 mm, YMC Co. Ltd., Japan). Sample size injected was 20 μl. Flow rate and operating pressure was 0.6 ml and c.1900 psi, respectively. Detection was 288 nm.

The results are given in Table 1 below.

TABLE 1

| Example | | Biotransformation products | |
|---|---|---|---|
| No. | Organism | II (%) | III (%) |
| 1 | *C. dalmatica* NRRL 1394 | 1.7 | 16.4 |
| 2 | *C. echinulata* NRRL 1387 | 1.9 | 23.6 |

TABLE 1-continued

| Example | | Biotransformation products | |
|---|---|---|---|
| No. | Organism | II (%) | III (%) |
| 3 | *C. echinulata* NRRL 1384 | 6.3 | 39.4 |
| 4 | *C. echinculata* ATCC 36190 | 15.8 | 19.2 |
| 5 | *C. echinculata* ATCC 11585a | 8.8 | 19.2 |
| 6 | *C. echinulata* ATCC 9244 | 10.2 | 21.7 |
| 7 | *C. polymorpha* NRRL 1395 | 10.4 | 31.5 |
| 8 | *R. nigracans* Z5/1 | — | 10.6 |

EXAMPLE 9

Each *Cunninghamella* type strain (see Table 2) was grown in a basal fermentation medium consisting of a single defined carbon source (glucose, sucrose, galactose or maltose) and a relatively undefined mixture of complex carbohydrates, amino acids and vitamins as contained in corn steep liquor. Biotransformations of compound I were carried out at 28° C. or 32° C. for 7 days and the results are summarised in Table 2.

Of the four strains tested, *C. echinulata* NRRL 1384 is a significantly better biocatalyst than the others with respect to both N-demethylation of compound I and N- and O-didemethylation of this same substrate. There is no significant difference between the levels of N-demethylation at either temperature, the mean conversions to product III being 55%±6.3% at 28° C. and 47%±6.5% at 32° C. respectively. However, didemethylation, to produce the product II, shows marked temperature dependence. At 28° C. the maximal formation of product II is approximately 20%. In contrast, at the elevated temperature of 32° C. formation of this compound can be inhibited by up to 53%, although changing the carbon source from glucose to galactose, maltose or sucrose can partially suppress this temperature dependence.

The other biocatalysts, *C. echinulata* ATCC 36190, *C. echinulata* NRRL 1387 and *C. echinulata* NRRL 1395, show no temperature dependence with respect to their ability to demethylate compound I. Although the N-demethylation pathways leading to the formation of product III are more active than the didemethylation pathways in these organisms, they are still at least 50% less active than the equivalent pathways in *C. echinulata* NRRL 1384.

TABLE 2

| STRAIN | SUGAR | 28° C. % II | 28° C. % III | 32° C. % II | 32° C. % III |
|---|---|---|---|---|---|
| ATCC36190 | Glucose | 11.2 ± 2.9 | 31.7 ± 6.2 | 11.6 ± 2.0 | 37.1 ± 7.7 |
| | Sucrose | 14.5 ± 0.8 | 33.6 ± 7.4 | 11.7 ± 0.5 | 36.2 ± 3.0 |
| | Galactose | 10.9[#] | 35.7[#] | 12.4 ± 0.9 | 37.5 ± 3.7 |
| | Maltose | 13.2 ± 0.3 | 35.3 ± 0.5 | 15.1 ± 1.9 | 46.2 ± 1.4 |
| NRRL1384 | Glucose | 20.5 ± 1.8 | 58.6 ± 1.6 | 9.5 ± 3.0 | 41.3 ± 8.3 |
| | Sucrose | 20.2 ± 1.2 | 53.9 ± 7.3 | 12.1 ± 1.3 | 42.4 ± 1.4 |
| | Galactose | 21.6 ± 1.1 | 61.7 ± 7.2 | 16.4 ± 1.5 | 55.0 ± 3.6 |
| | Maltose | 15.6 ± 1.1 | 47.2 ± 0.3 | 13.2 ± 1.7 | 50.0 ± 5.6 |
| NRRL1387 | Glucose | 6.5 ± 0.9 | 24.6 ± 5.4 | 5.4 +/− 0.3 | 23.1 +/− 0.6 |
| | Sucrose | 3.8 ± 2.4 | 13.5 ± 12.1 | 4.2 +/− 1.6 | 21.1 +/− 3.5 |
| | Galactose | 3.7 ± 0.4 | 11.6 ± 3.3 | 6.8 +/− 0.4 | 34.3 +/− 3.7 |
| | Maltose | 3.4 ± 0.4 | 12.1 ± 7.8 | 3.7 +/− 2.7 | 14.4 +/− 11.1 |
| NRRL1395 | Glucose | 6.9 ± 1.0 | 27.5 ± 3.6 | 5.6 ± 0.3 | 28.3 ± 0.6 |
| | Sucrose | 6.6 ± 0.2 | 25.5 ± 0.3 | 5.5 ± 0.1 | 24.5 ± 0.6 |
| | Galactose | 5.6 ± 0.6 | 26.8 ± 3.4 | 6.2 ± 0.6 | 31.2 ± 0.8 |
| | Maltose | 8.0 ± 1.2 | 29.3 ± 2.5 | 6.5 ± 0.3 | 28.3 ± 2.2 |

[#]n = 1 (n = 3 unless otherwise stated)

EXAMPLE 10

The effect of pH on *C. echinulata* NRRL 1384 mediated demethylation was assessed in GCM medium at 28° C. This medium was found to promote both N-demethylation and N- and O-didemethylation (data not shown) and this temperature was chosen in order for us to evaluate the effect of pH on both demethylation pathways without biasing the outcome of the biotransformation due to the temperature dependence previously identified. The data are summarised in Table 3. The optimum pH for promoting didemethylation is between pH5.0 and pH6.0 with the maximal formation of product II being 24.6%±6.3% at pH5.0. Above pH6.0 the efficiency of the process falls rapidly, whilst at more acidic pH's fungal growth, and hence biotransformation efficiency of the organism, is affected in an unpredictable way. This latter feature of the biotransformation process correlates with the observation that at pH3.0 fungal growth is completely inhibited.

N-demethylation of compound I operates over a broader pH range. The maximum formation of product III of 56.9%±14.2% is observed at pH5.0. However, mean product III levels of 44.4% and 50.3% at pH's 4.0 and 6.0 indicate that this pathway is robust and that N-demethylation of compound I is the biologically most favourable process in this organism.

TABLE III

| Initial pH | % Conversion III | % Conversion II |
|---|---|---|
| pH 3.0 (n = 3) | No growth | No growth |
| pH 4.0 | 16.0 ± 7.2 | 44.4 ± 3.8 |
| pH 5.0 | 24.6 ± 6.3 | 56.9 ± 14.2 |
| pH 6.0 | 21.0 ± 5.3 | 50.3 ± 8.9 |
| pH 7.0 (n = 3) | 11.6 ± 5.7 | 40.8 ± 11.0 |

N = 6 unless otherwise stated

The invention claimed is:

1. A process for the N-demethylation or the N- and O-demethylation of the compound of the formula

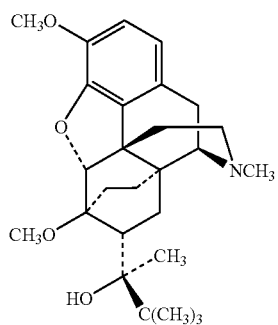

(I)

which process comprises fermenting the said compound of Formula I with a biocatalyst selected from the filamentous fungi from
*Cunninghamella dalmatica* NRRL 1394,
*Cunninghamella echinulata* NRRL 1387,
*Cunninghamella echinulata* NRRL 1384,
*Cunninghamella echinulata* ATCC 36190,
*Cunninghamella echinulata* ATCC 11585a,
*Cunninghamella echinulata* ATCC 9244,
*Cunninghamella polymorpha* NRRL 1395, or
*Rhizopus nigricans* Z5/1
in a basal fermentation medium at a temperature of at least 25° C. and not more than 34° C., for a period of time of at least 3 days.

2. A process according to claim 1 wherein the biocatalyst is *Cunninghamella echinulata* NRRL 1384.

3. A process according to claim 1 wherein the fermentation is carried out for a period of from 7 to 10 days.

4. A process according to claim 1 wherein the fermentation is carried out with vigorous shaking or stirring of the fermentation medium.

5. A process according to claim 1 wherein the fermentation medium comprises 2% w/v glucose, 0.5% w/v Corn Steep solids and has a pH of 6.2.

6. A process according to claim 1 wherein the N- or N- and O-demethylated products are separated from the fermentation medium by chromatography, crystallisation or extraction procedures.

7. A process according to claim 1 wherein the fermentation is carried out at a pH in the range of from 5 to 6.

8. A process for the preparation of buprenorphine, which process includes the step of the N-demethylation or the N- and O-demethylation of a compound of the formula

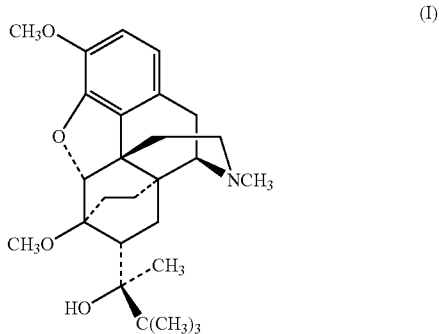

(I)

which process comprises fermenting the said compound of Formula I with a biocatalyst selected from the filamentous fungi
*Cunninghamella dalmatica* NRRL 1394,
*Cunninghamella echinulata* NRRL 1387,
*Cunninghamella echinulata* NRRL 1384,
*Cunninghamella echinulata* ATCC 36190,
*Cunninghamella echinulata* ATCC 11585a,
*Cunninghamella echinulata* ATCC 9244,
*Cunninghamella polymorpha* NRRL 1395, or
*Rhizopus nigricans* Z5/1
in a basal fermentation medium at a temperature of at least 25° C. and not more than 34° C. for a period of time of at least 3 days.

9. A process claim 8 wherein the compound produced by the N- and O-demethylation step is a compound having the following formula

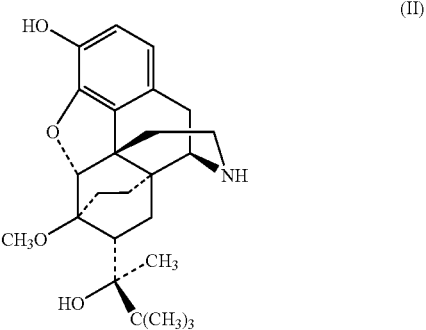

(II)

which is isolated from the fermentation medium and converted to buprenorphine by N-alkylation in order to introduce a cyclopropylmethyl group onto the N-atom.

10. A process according to claim 9 wherein the N-alkylation is carried out using a cyclopropylmethyl halide.

11. A process according to claim 8 wherein the compound produced by the N-demethylation step is a compound having the following formula

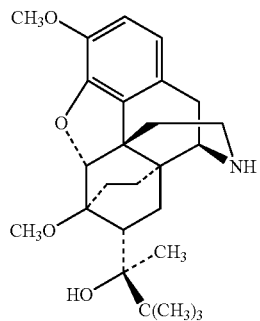

(III)

which is isolated from the fermentation medium and converted to buprenorphine by the following reaction stages:
(a) subjecting the compound of formula (III) to N-alkylation in order to introduce a cyclopropylmethyl group into the N-atom; and
(b) subjecting the compound produced in step (a) to O-demethylation in order to produce buprenorphine.

12. A process according to claim 11 wherein the N-alkylation is carried out using a cyclopropylmethyl halide.

13. A process according to as claimed in claim 11 wherein the O-demethylation is carried out with potassium hydroxide in diethylene glycol at an elevated temperature of from 200 to 245° C.

* * * * *

UNITED STATES PATENT AND TRADEMARK OFFICE
CERTIFICATE OF CORRECTION

PATENT NO. : 7,267,968 B2  
APPLICATION NO. : 10/512746  
DATED : September 11, 2007  
INVENTOR(S) : Andrew John Carnell et al.

It is certified that error appears in the above-identified patent and that said Letters Patent is hereby corrected as shown below:

Title page item (73),
    Under the heading "Assignee":
    Reckitt Benekiser Healthcare (UK) Limited, Slough, Berkshire (GB)

should read:
    Reckitt Benckiser Healthcare (UK) Limited, Slough, Berkshire (GB)

Signed and Sealed this

Eighteenth Day of March, 2008

JON W. DUDAS  
*Director of the United States Patent and Trademark Office*

UNITED STATES PATENT AND TRADEMARK OFFICE
CERTIFICATE OF CORRECTION

PATENT NO. : 7,267,968 B2
APPLICATION NO. : 10/512746
DATED : September 11, 2007
INVENTOR(S) : Carnell et al.

Page 1 of 1

It is certified that error appears in the above-identified patent and that said Letters Patent is hereby corrected as shown below:

Column 8, line 46, "A process claim 8" should read -- A process according to claim 8 --

Column 10, line 11, "A process according to as claimed in claim 11" should read -- A process according to claim 11 --

Signed and Sealed this

Second Day of December, 2008

JON W. DUDAS
*Director of the United States Patent and Trademark Office*